United States Patent
Nguyen (10) Patent No.: US 11,950,793 B2
(45) Date of Patent: *Apr. 9, 2024

(54) DEVICE AND METHOD FOR GENERATING FORWARD DIRECTED SHOCK WAVES

(71) Applicant: Shockwave Medical, Inc., Santa Clara, CA (US)

(72) Inventor: Hoa D. Nguyen, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/106,900

(22) Filed: Feb. 7, 2023

(65) Prior Publication Data
US 2023/0190316 A1 Jun. 22, 2023

Related U.S. Application Data

(63) Continuation of application No. 17/185,276, filed on Feb. 25, 2021, now Pat. No. 11,602,363, which is a
(Continued)

(51) Int. Cl.
*A61B 17/22* (2006.01)
*A61M 5/00* (2006.01)
*A61M 25/10* (2013.01)

(52) U.S. Cl.
CPC .... *A61B 17/22022* (2013.01); *A61B 17/2202* (2013.01); *A61M 5/007* (2013.01);
(Continued)

(58) Field of Classification Search
CPC .......... A61B 2017/22025; A61B 2017/22001; A61B 17/22012; A61B 17/22022; A61B 17/22029; A61B 17/22004
See application file for complete search history.

(56) References Cited

U.S. PATENT DOCUMENTS

| 3,413,976 A | 12/1968 | Voolfovich |
| 3,785,382 A | 1/1974 | Schmidt et al. |

(Continued)

FOREIGN PATENT DOCUMENTS

| AU | 2009313507 B2 | 11/2014 |
| CN | 1204242 A | 1/1999 |

(Continued)

OTHER PUBLICATIONS

Advisory Action received for U.S. Appl. No. 13/615,107, mailed on Nov. 6, 2015, 3 pages.
(Continued)

*Primary Examiner* — Majid Jamialahmadi
(74) *Attorney, Agent, or Firm* — Morrison & Foerster LLP (57) ABSTRACT

Described herein is a shock wave device for the treatment of vascular occlusions. The shock wave device includes an outer covering and an inner member inner connected at a distal end of the device. First and second conductive wires extend along the length of the device within the volume between the outer covering and the inner member. A conductive emitter band circumscribes the ends of the first and second wires to form a first spark gap between the end of the first wire and the emitter band and a second spark gap between the end of the second wire and the emitter band. When the volume is filled with conductive fluid and a high voltage pulse is applied across the first and second wires, first and second shock waves can be initiated from the first and second spark gaps.

15 Claims, 6 Drawing Sheets

Related U.S. Application Data continuation of application No. 15/989,016, filed on May 24, 2018, now Pat. No. 10,966,737.

(60) Provisional application No. 62/521,994, filed on Jun. 19, 2017.

(52) U.S. Cl.
CPC ............... *A61M 25/10181* (2013.11); *A61M 25/10186* (2013.11); *A61M 25/104* (2013.01); *A61B 2017/22001* (2013.01); *A61B 2017/22025* (2013.01); *A61B 2017/22028* (2013.01); *A61B 2017/22038* (2013.01); *A61B 2017/22051* (2013.01); *A61B 2017/22062* (2013.01); *A61M 2025/1079* (2013.01); *A61M 2210/1082* (2013.01); *A61M 2210/12* (2013.01)

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,030,505 A | 6/1977 | Tessler |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,813,934 A | 3/1989 | Engelson et al. |
| 4,878,495 A | 11/1989 | Grayzei |
| 4,900,303 A | 2/1990 | Lemeison |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,103,804 A | 4/1992 | Abele et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,231,976 A | 8/1993 | Wiksell |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,431,173 A | 7/1995 | Chin et al. |
| 5,472,406 A | 12/1995 | De La Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | De La Torre et al. |
| 5,846,218 A | 12/1998 | Brisken et al. |
| 5,931,805 A | 8/1999 | Brisken |
| 6,007,530 A | 12/1999 | Domhofer et al. |
| 6,024,718 A | 2/2000 | Chen et al. |
| 6,033,371 A | 3/2000 | Torre et al. |
| 6,080,119 A | 6/2000 | Schwarze et al. |
| 6,083,232 A | 7/2000 | Cox |
| 6,113,560 A | 9/2000 | Simnacher |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,124 B1 | 8/2002 | Esch et al. |
| 6,514,203 B2 | 2/2003 | Bukshpan |
| 6,524,251 B2 | 2/2003 | Rabiner et al. |
| 6,589,253 B1 | 7/2003 | Comish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,505,812 B1 | 3/2009 | Eggers et al. |
| 7,569,032 B2 | 8/2009 | Naimark et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,522,012 B2 | 12/2016 | Adams |
| 9,730,715 B2 | 8/2017 | Adams |
| 9,993,292 B2 | 6/2018 | Adams et al. |
| 10,159,505 B2 | 12/2018 | Hakala et al. |
| 10,226,265 B2 | 3/2019 | Ku et al. |
| 10,517,620 B2 | 12/2019 | Adams |
| 10,517,621 B1 | 12/2019 | Adams |
| 10,555,744 B2 | 2/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,534,187 B2 | 12/2022 | Bonutti |
| 11,596,424 B2 | 3/2023 | Hakala et al. |
| 11,602,363 B2 | 3/2023 | Nguyen |
| 11,622,780 B2 | 4/2023 | Nguyen et al. |
| 11,696,799 B2 | 7/2023 | Adams et al. |
| 2001/0044596 A1 | 11/2001 | Jaafar |
| 2002/0045890 A1 | 4/2002 | Celliers et al. |
| 2002/0177889 A1 | 11/2002 | Brisken et al. |
| 2003/0004434 A1 | 1/2003 | Greco et al. |
| 2003/0060813 A1 | 3/2003 | Loeb et al. |
| 2003/0176873 A1 | 9/2003 | Chernenko et al. |
| 2003/0229370 A1 | 12/2003 | Miller |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |

(56) References Cited

U.S. PATENT DOCUMENTS

| | | |
|---|---|---|
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0074484 A1 | 4/2006 | Huber |
| 2006/0184076 A1 | 8/2006 | Gm et al. |
| 2006/0190022 A1 | 8/2006 | Beyar et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0255270 A1 | 11/2007 | Camey |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2008/0294037 A1 | 11/2008 | Ritcher |
| 2009/0041833 A1 | 2/2009 | Bettinger et al. |
| 2009/0227992 A1 | 9/2009 | Nir et al. |
| 2009/0234282 A1 | 9/2009 | McAndrew et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0022950 A1 | 1/2010 | Anderson et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1* | 5/2010 | Hawkins ......... A61B 17/22022 604/509 |
| 2010/0121322 A1 | 5/2010 | Swanson |
| 2010/0125244 A1 | 5/2010 | McAndrew |
| 2010/0274189 A1 | 10/2010 | Kurth et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0203255 A1 | 8/2012 | Hawkins et al. |
| 2012/0221013 A1 | 8/2012 | Hawkins et al. |
| 2012/0271339 A1 | 10/2012 | O'beirne et al. |
| 2013/0030431 A1 | 1/2013 | Adams |
| 2014/0039513 A1 | 2/2014 | Hakala et al. |
| 2014/0052147 A1 | 2/2014 | Hakala et al. |
| 2014/0350401 A1 | 11/2014 | Sinelnikov |
| 2015/0073430 A1 | 3/2015 | Hakala et al. |
| 2015/0238209 A1 | 8/2015 | Hawkins et al. |
| 2015/0320432 A1 | 11/2015 | Adams |
| 2016/0151081 A1 | 6/2016 | Adams et al. |
| 2016/0174995 A1 | 6/2016 | Turjman et al. |
| 2016/0324534 A1 | 11/2016 | Hawkins et al. |
| 2017/0135709 A1 | 5/2017 | Nguyen et al. |
| 2017/0151415 A1 | 6/2017 | Maeda et al. |
| 2017/0311965 A1 | 11/2017 | Adams |
| 2018/0098779 A1 | 4/2018 | Betelia et al. |
| 2019/0365400 A1 | 12/2019 | Adams et al. |
| 2021/0085347 A1 | 3/2021 | Phan et al. |
| 2021/0085383 A1 | 3/2021 | Vo et al. |
| 2021/0282792 A1 | 9/2021 | Adams et al. |
| 2021/0338258 A1 | 11/2021 | Hawkins et al. |
| 2022/0015785 A1 | 1/2022 | Hakala et al. |
| 2022/0183708 A1 | 6/2022 | Phan et al. |
| 2022/0240958 A1 | 8/2022 | Nguyen et al. |
| 2023/0043475 A1 | 2/2023 | Adams |

FOREIGN PATENT DOCUMENTS

| | | |
|---|---|---|
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102765785 A | 11/2012 |
| CN | 103068330 A | 4/2013 |
| CN | 203564304 U | 4/2014 |
| CN | 104582621 A | 4/2015 |
| CN | 104736073 A | 6/2015 |
| CN | 105188848 A | 12/2015 |
| DE | 3038445 A1 | 5/1982 |
| EP | 442199 A2 | 8/1991 |
| EP | 571306 A1 | 11/1993 |
| EP | 623360 A1 | 11/1994 |
| EP | 1596746 A2 | 11/2005 |
| EP | 2253884 A1 | 11/2010 |
| EP | 2362798 B1 | 4/2014 |
| EP | 3434209 A1 | 1/2019 |
| EP | 3473195 A1 | 4/2019 |
| JP | S60-191353 U | 12/1985 |
| JP | S61-135648 A | 6/1986 |
| JP | S62-099210 U | 6/1987 |
| JP | S62-275446 A | 11/1987 |
| JP | H3-63059 A | 3/1991 |
| JP | H06-125915 A | 5/1994 |
| JP | H07-47135 A | 2/1995 |
| JP | H08-89511 A | 4/1996 |
| JP | H10-314177 A | 12/1998 |
| JP | 2002538932 A | 11/2002 |
| JP | 2004081374 A | 3/2004 |
| JP | 2004357792 A | 12/2004 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011520248 A | 7/2011 |
| JP | 2011524203 A | 9/2011 |
| JP | 2011528963 A | 12/2011 |
| JP | 2012505050 A | 3/2012 |
| JP | 2012508042 A | 4/2012 |
| JP | 2014208305 A | 11/2014 |
| JP | 2015525657 A | 9/2015 |
| JP | 2015528327 A | 9/2015 |
| JP | 6029828 B2 | 11/2016 |
| JP | 6081510 B2 | 2/2017 |
| JP | 2020524032 A | 8/2020 |
| WO | WO-1992003975 A1 | 3/1992 |
| WO | WO-1996024297 A1 | 8/1996 |
| WO | WO-1999002096 A1 | 1/1999 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009152352 A2 | 12/2009 |
| WO | WO-2010014515 A2 | 2/2010 |
| WO | WO-2010014515 A3 | 8/2010 |
| WO | WO-2010054048 A3 | 9/2010 |
| WO | WO-2011143468 A2 | 11/2011 |
| WO | WO-2012025833 A2 | 3/2012 |
| WO | WO-2013169807 A1 | 11/2013 |
| WO | WO-2016077627 A1 | 5/2016 |

(56) References Cited

FOREIGN PATENT DOCUMENTS

| WO | WO-2016109739 A1 | 7/2016 |
|----|------------------|--------|
| WO | WO-2019099218 A1 | 5/2019 |

OTHER PUBLICATIONS

Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Advisory Action Received for U.S. Appl. No. 12/581,295, mailed on Jul. 3, 2014, 3 pages.
Advisory Action Received for U.S. Appl. No. 13/049,199, mailed on Jun. 7, 2012, 3 pages.
Advisory Action received for U.S. Appl. No. 13/267,383, mailed on Jan. 6, 2014, 4 pages.
Advisory Action received for U.S. Appl. No. 17/021,905, mailed on Nov. 22, 2022, 4 pages.
Decision of Appeals Notice received for Japanese Patent Application No. 2011-534914, mailed on Oct. 17, 2016, 2 pages of Official Copy only.
Decision to Grant received for European Patent Application No. 13756766.5, mailed on May 27, 2016, 2 pages.
Decision to Grant received for European Patent Application No. 09825393.3, mailed on Mar. 13, 2014, 2 pages.
Extended European Search Report (includes Supplementary European Search Report and Search Opinion) received for European Patent Application No. 09763640.1, mailed on Oct. 10, 2013, 5 pages.
Extended European Search Report and Search Opinion received for European Patent Application No. 09825393.3, mailed on Feb. 28, 2013, 6 pages.
Extended European Search Report received for European Patent Application No. 13827971.6, mailed on Apr. 12, 2016, 8 pages.
Extended European Search Report received for European Patent Application No. 21191690.3, mailed on Jan. 17, 2022, 3 pages.
Final Office Action received for U.S. Appl. No. 12/482,995, mailed on Jul. 22, 2011, 14 pages.
Final Office Action received for U.S. Appl. No. 12/501,619, mailed on Feb. 21, 2012, 12 pages.
Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 13/049,199, mailed on Apr. 4, 2012, 10 pages.
Final Office Action received for U.S. Appl. No. 13/207,381, mailed on Nov. 2, 2012, 7 pages.
Final Office Action received for U.S. Appl. No. 14/271,342 mailed on Feb. 27, 2015, 7 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 12/611,997, mailed on Oct. 24, 2013 10 pages.
Final Office Action received for U.S. Appl. No. 13/049,199 mailed on Aug. 11, 2014, 8 pages.
Final Office Action received for U.S. Appl. No. 13/207,381, mailed on Nov. 7, 2013 7 pages.
Final Office Action Received for U.S. Appl. No. 13/267,383, mailed on May 28, 2015, 12 pages.
Final Office Action received for U.S. Appl. No. 13/267,383, mailed on Oct. 25, 2013 8 pages.
Final Office Action received for U.S. Appl. No. 13/534,658, mailed on Aug. 23, 2016, 11 pages.
Final Office Action received for U.S. Appl. No. 13/615,107 mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/229,735, mailed on Aug. 27, 2015, 7 pages.
Final Office Action received for U.S. Appl. No. 14/273,063, mailed on Dec. 28, 2016, 11 pages.
Final Office Action received for U.S. Appl. No. 14/660,539, mailed on Aug. 3, 2017, 11 pages.
Final Office Action received for U.S. Appl. No. 17/021,905, mailed on Sep. 12, 2022, 11 pages.
Intention to Grant received for European Patent Application No. 13756766.5, mailed on Jan. 8, 2016, 5 pages.
International Preliminary Report on Patentability received for PCT Patent Application No. PCT/US2009/047070, mailed on Dec. 23, 2010, 7 pages.
International Preliminary Report on Patentability received for PCT Patent Application No. PCT/US2009/063354, mailed on May 19, 2011, 6 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 mailed on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533 mailed on Mar. 26, 2015, 10 pages.
International Preliminary Report on Patentability received for PCT Patent Application No. PCT/US2015/029088, mailed on Nov. 17, 2016, 8 pages.
International Search Report and Written Opinion Received for PCT Application No. PCT/US2018/034855, mailed on Aug. 23, 2018, 13 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088 mailed on Jul. 16, 2015, 13 pages.
International Search Report and Written Opinion received for PCT Patent Application No. PCT/US2020/050899 mailed on Feb. 2, 2021, 19 pages.
International Search Report received for PCT Patent Application No. PCT/US2009/047070, mailed on Jan. 19, 2010, 4 pages.
International Search Report received for PCT Patent Application No. PCT/US2009/063354, mailed on Jun. 11, 2010, 3 pages.
International Search Report received for PCT Patent Application No. PCT/US2012/023172, mailed on Sep. 28, 2012, 3 pages.

(56) References Cited

OTHER PUBLICATIONS

International Search Report received for PCT Patent Application No. PCT/US2021/062666 mailed on Mar. 25, 2022, 9 pages.
International Written Opinion received for PCT Patent Application No. PCT/US2009/063354, mailed on Jun. 11, 2010, 4 pages.
International Written Opinion received for PCT Patent Application No. PCT/US2011/047070, mailed on May 1, 2012, 5 pages.
Invitation to Pay Additional Fees for PCT Patent Application No. PCT/US2020/050899, mailed on Nov. 5, 2020, 16 pages.
Non Final Office Action received for U.S. Appl. No. 12/482,995, mailed on Aug. 13, 2014, 10 pages.
Non Final Office Action received for U.S. Appl. No. 12/482,995, mailed on Jul. 12, 2013, 11 pages.
Non Final Office Action received for U.S. Appl. No. 12/611,997, mailed on Nov. 26, 2014, 8 pages.
Non Final Office Action received for U.S. Appl. No. 13/207,381, mailed on Nov. 25, 2014, 5 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non Final Office Action received for U.S. Appl. No. 14/079,463, mailed on Mar. 4, 2014, 9 pages.
Non Final Office Action received for U.S. Appl. No. 12/482,995, mailed on Feb. 11, 2011, 27 pages.
Non Final Office Action received for U.S. Appl. No. 12/501,619, mailed on Nov. 3, 2011, 10 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non Final Office Action received for U.S. Patent Application No. 13/049, 199, mailed on Dec. 12, 2011, 10 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non Final Office Action received for U.S. Appl. No. 13/534,658, mailed on Mar. 11, 2016, 12 pages.
Non Final Office Action received for U.S. Appl. No. 14/218,858, mailed on Mar. 30, 2016, 13 pages.
Non Final Office Action received for U.S. Appl. No. 14/515,130, mailed on Jan. 14, 2016, 16 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 12/611,997, mailed on Feb. 13, 2014, 9 pages.
Non-Final Office Action received for U.S. Patent Application No. 13/049, 199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Patent Application No. 13/615, 107, mailed on Apr. 24, 2015, 9 pages.
Non-Final Office Action received for U.S. Appl. No. 13/646,583, mailed on Oct. 31, 2014, 8 pages.
Non-Final Office Action received for U.S. Appl. No. 14/061,554, mailed on Mar. 12, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/660,539, mailed on Mar. 6, 2017, 14 pages.
Non-Final Office Action received for U.S. Appl. No. 14/660,539, mailed on Nov. 24, 2017, 10 pages.
Non-Final Office Action received for U.S. Patent Application No. 14/693, 155, mailed on Jan. 15, 2016, 6 pages.
Non-Final Office Action received for U.S. Appl. No. 17/021,905, mailed on Apr. 8, 2022, 11 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.
Notice of Allowance received for Canadian Patent Application No. 2,727,429, mailed on May 26, 2015, 1 page.
Notice of Allowance received for Canadian Patent Application No. 2,779,600, mailed on Jul. 7, 2017, 1 page.
Notice of Allowance received for Japanese Patent Application No. 2015-036444, mailed on Jan. 13, 2017, 3 pages (Official Copy Only).
Notice of Allowance received for U.S. Patent Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 12/611,997, mailed on Apr. 15, 2015, 7 pages.
Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/957,276, mailed on Aug. 28, 2015, 9 pages.
Notice of Allowance received for U.S. Appl. No. 14/271,276, mailed on Feb. 25, 2015, 8 pages.
Notice of Allowance received for U.S. Appl. No. 12/482,995, mailed on Dec. 24, 2014, 6 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,342, mailed on Mar. 13, 2015, 5 pages.
Notice of Allowance received for U.S. Appl. No. 14/273,063, mailed on Apr. 12, 2017. 7 pages.
Notice of Allowance received for U.S. Appl. No. 14/660,539, mailed on Apr. 6, 2018, 7 pages.
Notice of Allowance received for U.S. Appl. No. 14/693,155, mailed on Apr. 26, 2016, 9 pages.
Notice of Allowance received for U.S. Appl. No. 17/185,276, mailed on Jan. 4, 2023, 8 pages.
Notice of Allowance received for U.S. Appl. No. 17/185,276, mailed on Oct. 26, 2022, 10 pages.
Notice of Allowance received for U.S. Appl. No. 13/615,107, mailed on Dec. 31, 2015, 10 pages.

(56) References Cited

OTHER PUBLICATIONS

Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2009313507, mailed on Nov. 13, 2013, 3 pages.
Office Action received for Canadian Patent Application No. 2,727,429, mailed on Apr. 14, 2015, 4 pages.
Office Action received for Canadian Patent Application No. 2,779,600, mailed on Jan. 4, 2016, 6 pages.
Office Action received for Canadian Patent Application No. 2,779,600, mailed on Oct. 19, 2016, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages (Official copy only).
Office Action received for Chinese Patent Application No. 201380033808.3, mailed on Jul. 5, 2016. 9 pages (3 pages of English translation and 6 pages of Official copy).
Office Action received for Chinese Patent Application No. 201380041656.1, mailed on Jul. 5, 2016. 9 pages (4 pages of English translation and 5 pages of Official copy).
Office Action received for Chinese Patent Application No. 201380042887.4, mailed on Aug. 8, 2016, 9 pages (4 pages of English translation and 5 pages of Official copy).
Office Action received for Chinese Patent Application No. 201880040835.6, mailed on Oct. 14, 2022, 8 pages.
Office Action received for European Patent Application No. 09763640.1, mailed on Dec. 2, 2016, 4 pages.
Office Action received for Japanese Patent Application No. 2011-513694, mailed on Aug. 27, 2013, 6 pages (3 pages of English Translation and 3 pages of Official copy).
Office Action Received for Japanese Patent Application No. 2011-513694, mailed on Jun. 10, 2014, 4 pages total (2 pages of Official Copy and 2 pages of English Translation) .
Office Action Received for Japanese Patent Application No. 2011-534914, mailed on Jan. 13, 2015, 9 pages(7 pages of English Translation and 2 pages of Official Copy.
Office Action received for Japanese Patent Application No. 2011-534914, mailed on May 10, 2016, 10 pages ( 4 pages of Official Copy and 6 pages of English Translation).
Office Action received for Japanese Patent Application No. 2011-534914, mailed on Oct. 1, 2013, 5 pages (2 pages of English Translation and 3 pages of Official copy).
Office Action received for Japanese Patent Application No. 2014-158517, mailed on Feb. 15, 2017, 8 pages (5 pages of English Translation and 3 pages of Official Copy Only).
Office Action Received for Japanese Patent Application No. 2014-158517, mailed on Jun. 22, 2017. 14 pages of official Copy only.
Office Action Received for Japanese Patent Application No. 2014-158517, mailed on May 19, 2015, 5 pages (2 pages of English Translation and 3 pages of Official Copy).
Office Action received for Japanese Patent Application No. 2015-036444, mailed on Feb. 23, 2016, 3 pages of English translation only.
Office Action received for Japanese Patent Application No. 2016-143049, mailed on Apr. 24, 2017. 5 pages ( 2 pages of English Translation and 3 pages of Official copy).
Office Action received for Japanese Patent Application No. 2019-569918, mailed on Feb. 14, 2022, 6 pages. English translation.
Office Action received for Japanese Patent Application No. 2015-036444, mailed on Sep. 14, 2016, 5 pages (3 Pages of English Translation and 2 Pages of Official Copy).
Office Action received for Japanese Patent Application No. 2016-094326, mailed on Dec. 2, 2016, 4 pages (2 pages of English Translation and 2 pages Official Copy Only).
Office Action received for Japanese Patent Application No. 2016-094326, mailed on Jul. 6, 2017, 2 pages (Official Copy Only).
Requirement for Restriction/Election received for U.S. Appl. No. 17/021,905 mailed on Nov. 8, 2021, 5 pages.
Rosenschein et al., (1992). "Shock-Wave Thrombus Ablation, a New Method for Noninvasive Mechanical Thrombolysis," The American Journal of Cardiology, 70:1358- 1361.
Third Party Preissuance Submission for U.S. Appl. No. 15/989,016, filed on Mar. 8, 2019, 3 pages.
Zhong et al., (1997). "Transient Oscillation of Cavitation Bubbles Near Stone Surface During Electrohydraulic Lithotripsy," Journal of Endourology, 11:55-61.

* cited by examiner

DEVICE AND METHOD FOR GENERATING FORWARD DIRECTED SHOCK WAVES

PRIORITY

This application is a continuation of U.S. application Ser. No. 17/185,276, filed Feb. 25, 2021, which is a continuation of U.S. application Ser. No. 15/989,016, filed May 24, 2018, now U.S. Pat. No. 10,966,737, issued Apr. 6, 2021, which in turn claims priority to provisional Application No. 62/521,994, filed Jun. 19, 2017, the entire disclosures of each of which are incorporated by reference.

FIELD

The present disclosure relates generally to the generation of shock waves, and, more specifically, to the generation of shock waves within vascular or urinary structures.

BACKGROUND

The subject invention relates to treating calcified lesions in blood vessels, or obstructions in other vessels, such as kidney stones in ureters. One common approach to addressing this issue is balloon angioplasty. In this type of procedure, a catheter, carrying a balloon, is advanced into the vasculature along a guide wire until the balloon is aligned with the occlusion. The balloon is then pressurized in a manner to reduce or break the occlusion. When inflated to high pressures, angioplasty balloons can have a specific maximum diameter to which they will expand. Generally, the opening in the vessel under a concentric lesion will typically be much smaller. As the pressure is increased to open the passage way for blood flow, the balloon will be confined to the size of the opening in the calcified lesion (before it is broken open). As the pressure builds, a tremendous amount of energy is stored in the balloon until the calcified lesion breaks or cracks. That energy is then released and results in the rapid expansion of the balloon to its maximum dimension and may stress and injure the vessel walls.

Recently, the assignee herein has developed a system and method for breaking up calcium deposits in, for example, arteries and veins. Such a system is described, for example in U.S. Pat. Nos. 8,956,371 and 8,888,788, both of which are incorporated herein by reference. Embodiments described therein include a catheter having balloon, such as an angioplasty balloon, at the distal end thereof arranged to be inflated with a fluid. Disposed within the balloon is a shock wave generator that may take the form of, for example, a pair of electrodes, which are coupled to a high voltage source at the proximal end of the catheter through a connector. When the balloon is placed adjacent a calcified region of a vein or artery and a high voltage pulse is applied across the electrodes, a shock wave is formed that propagates through the fluid and impinges upon the wall of the balloon and the calcified region. Repeated pulses break up the calcium without damaging surrounding soft tissue. A similar technique can be used to treat kidney stones in the ureter. The shock waves generated by such systems typically propagate in all directions from the electrodes.

Arteries are sometimes totally occluded with a thrombus, plaque, fibrous plaque, and/or calcium deposits. When this condition is present, the physician typically first passes a soft narrow guide wire down the artery and through the occluded area. The guide wire may be as small as 0.014 inches in diameter and usually has a soft flexible tip to help avoid penetrating the artery wall in artery corners. The angioplasty balloon is then fed down the artery on the guide wire to the desired location of the blockage. Unfortunately, many times the physician is faced with a chronic occlusion which is not passable with a guide wire. This occurs when the occlusion is so tight and solid that the soft guide wire cannot penetrate through it. Stiffer guide wires may be used in these cases, but they must be used very carefully because they can easily penetrate the artery wall when forced against the chronic total occlusion.

Guide wires have been proposed that utilize radio frequency energy to open the occlusion. Unfortunately, the heat generated by the radio frequency energy to open the occlusion is intense and can damage the walls of the artery or vessel. The radio frequency energy produces a plasma which burns anything in its path. Hence, such systems must be used carefully and must be continuously moved without pause to avoid artery or vessel damage. Moreover, such an approach requires a centering mechanism that keeps the plasma centered in the artery or vessel. Such centering is difficult to achieve, especially in the corners and bends of the arteries or veins.

More recently, the assignee herein has proposed providing an electrode on the tip of a guide wire for generating forward directed shock waves to open a total occlusion enough to permit a guide wire and angioplasty balloon to be fed there through. In addition, such system avoids damage to the artery or vessel. This approach is disclosed in U.S. Patent Publication No. 2015/0320432, also incorporated herein by reference.

The subject invention relates to yet another alternative approach for generating forward directed shock waves that can be integrated with an angioplasty balloon. This approach can also be used in conjunction with other types of shock wave electrodes.

BRIEF SUMMARY

Described herein are shock wave devices and methods for the treatment of plaques or obstructions in vessels. The vessels may include blood vessels in a patient's vascular system or ureters in the patient's urinary system. One example of a shock wave device includes an outer covering and an inner member forming a guide wire lumen. The outer covering and inner member are connected at a distal end of the device, and a volume between the outer covering and the inner member is fillable with a conductive fluid. A first conductive wire and a second conductive wire extend along the length of the device within the volume between the outer covering and the inner member and end proximate to the distal end of the device. The lengths of the first and second wires are insulated and the ends of the first and second wires are uninsulated. A conductive emitter band circumscribes the ends of the first and second wires and forms a first spark gap between the end of the first wire and the emitter band and a second spark gap between the end of the second wire and the emitter band. When the volume is filled with the conductive fluid and a high voltage pulse is applied across the first and second wires, first and second shock waves will be initiated from the first and second spark gaps.

In some examples, the device further includes an insulting sheath circumscribing the inner member in a region proximate to the ends of the first and second wires. In some variations, the outer covering comprises an angioplasty balloon. In some examples, the emitter band is a cylindrical tube that extends closer to the distal end of the device than the first and second wires. In some examples, the device further includes a fluid pump connected to a proximal end of the device configured to provide conductive fluid to the volume between the outer covering and the inner member, and a fluid return line having an inlet proximate to the distal end of the device and configured to remove the conductive fluid from the volume between the outer covering and the inner member. The fluid pump and fluid return line may be configured to circulate the conductive fluid under pressure within the volume between the outer covering and the inner member. In some examples, the device further includes a pressure relief valve at an outlet of the fluid return line.

In some examples, the device further includes a third conductive wire and a fourth conductive wire extending along the length of the device within the volume between the outer covering and the inner member and ending proximate to the distal end of the device. The lengths of the third and fourth wires may be insulated and the ends of the third and fourth wires may be uninsulated. The conductive emitter band may circumscribe the ends of the third and fourth wires and form a third spark gap between the end of the third wire and the emitter band and a fourth spark gap between the end of the fourth wire and the emitter band. When the volume is filled with the conductive fluid and a second high voltage pulse is applied across the third and fourth wires, third and fourth shock waves may be initiated from the third and fourth spark gaps. In some examples, the conductive fluid comprises saline or a combination of saline and a contrasting agent. In some examples, the device further includes one or more secondary emitter bands disposed at a medial location of the device and configured to initiate at least a third shock wave from the medial location.

One example of a method includes introducing a shock wave device into a vessel, advancing the shock wave device within the vessel such that a distal end of the shock wave device faces a first treatment region, and applying a high voltage pulse across first and second wires to initiate first and second shock waves from first and second spark gaps formed between the first and second wires and an emitter band. The positioning of the first and second wires and the emitter band results in the first and second shock waves propagating in a substantially forward direction.

In some examples, the method further includes, after the applying step, advancing the shock wave device further within the vessel such that an angioplasty balloon is aligned with the first treatment region or second treatment region, and inflating the angioplasty balloon. In some examples, the method further includes, after the applying step, advancing the shock wave device further within the vessel such that one or more secondary emitter bands at a medial location of the device are aligned with the first treatment region or a second treatment region, and initiating third shock waves from the secondary emitter bands. In some examples, the vessel is a blood vessel of a patient's vascular system or a ureter of the patient's urinary system. In some examples, first treatment region includes a chronic total occlusion (CTO), circumferential calcium, or a kidney stone.

DETAILED DESCRIPTION

Described herein are devices, systems, and methods for generating shock waves that propagate in a substantially forward direction to treat vascular diseases, such as chronic total occlusion (CTO) or circumferential calcium, or to treat urinary diseases, such as concretions or kidney stones in the ureter. In accordance with the present disclosure, a shock wave device includes an outer covering and an inner member forming a guide wire lumen. The outer covering and inner member are connected at a distal end of the device. A first conductive wire and a second conductive wire extend along the length of the device within the volume between the outer covering and the inner member, and end proximate to the distal end of the device. A conductive emitter band circumscribes the ends of the first and second wires to form a first spark gap between the end of the first wire and the emitter band and a second spark gap between the end of the second wire and the emitter band.

When the volume is filled with conductive fluid (e.g., saline and/or imaging contrast agent) and a high voltage pulse is applied across the first and second wires, first and second shock waves can be initiated from the first and second spark gaps. The voltage may range from 100 to 10,000 volts for various pulse durations. This high voltage may generate a gas bubble at the end surface of a wire and cause a plasma arc of electric current to traverse the bubble to the emitter band and create a rapidly expanding and collapsing bubble, which in turn creates a mechanical shock wave at the distal end of the device. The positioning of the emitter band in relation to the end of the wire may result in the shock wave propagating out in a substantially forward direction toward the distal end of the device. The shock waves may be mechanically conducted through the conductive fluid and through the outer covering in the substantially forward direction to apply mechanical force or pressure to impinge on an occlusion or calcium facing the distal end of the device. The size, rate of expansion and collapse of the bubble (and therefore, the magnitude, duration, and distribution of the mechanical force) may vary based on the magnitude and duration of the voltage pulse, as well as the distance between the end of the wire and the emitter band. The emitter band may be made of materials that can withstand high voltage levels and intense mechanical forces (e.g., about 1000-2000 psi or 68-136 ATM in a few microseconds) that are generated during use. For example, the emitter band may be made of stainless steel, tungsten, nickel, iron, steel, and the like.

Figure 1:
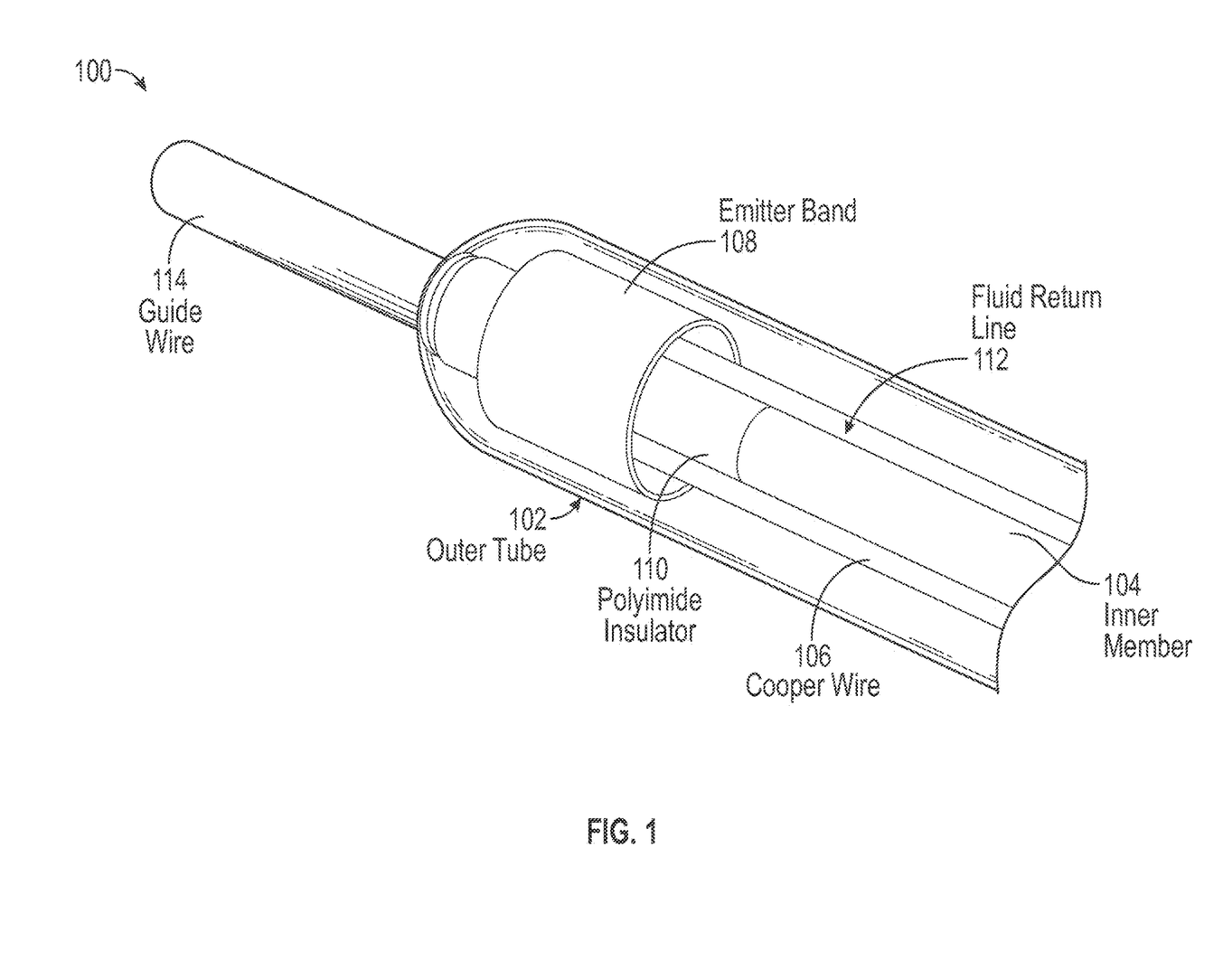
FIG. 1 depicts a cutaway perspective view of an example shock wave device for generating forward directed shock waves, in accordance with some embodiments.
Figure 2:
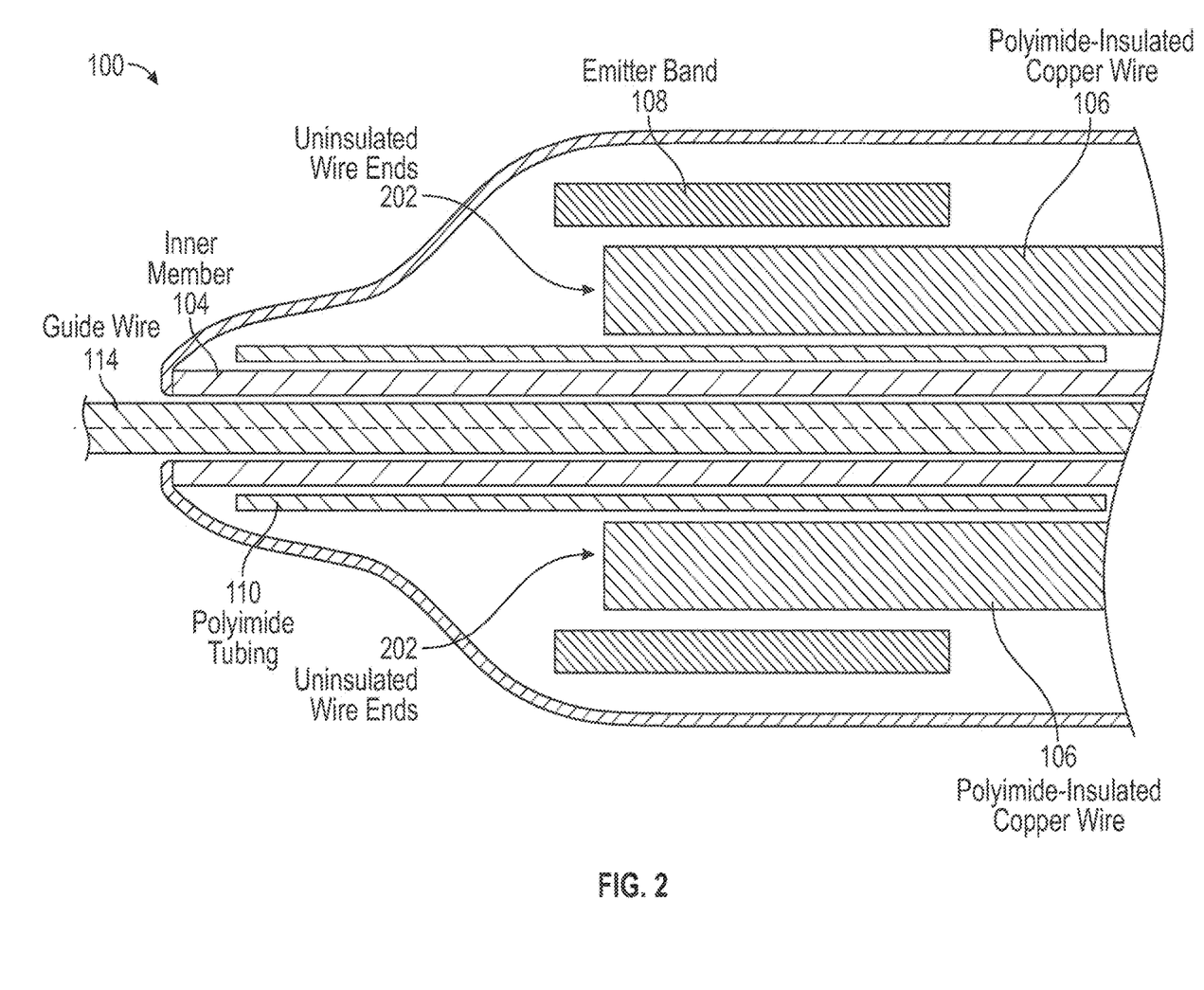
FIG. 2 depicts a side sectional view of an example shock wave device for generating forward directed shock waves, in accordance with some embodiments.
Figure 3:
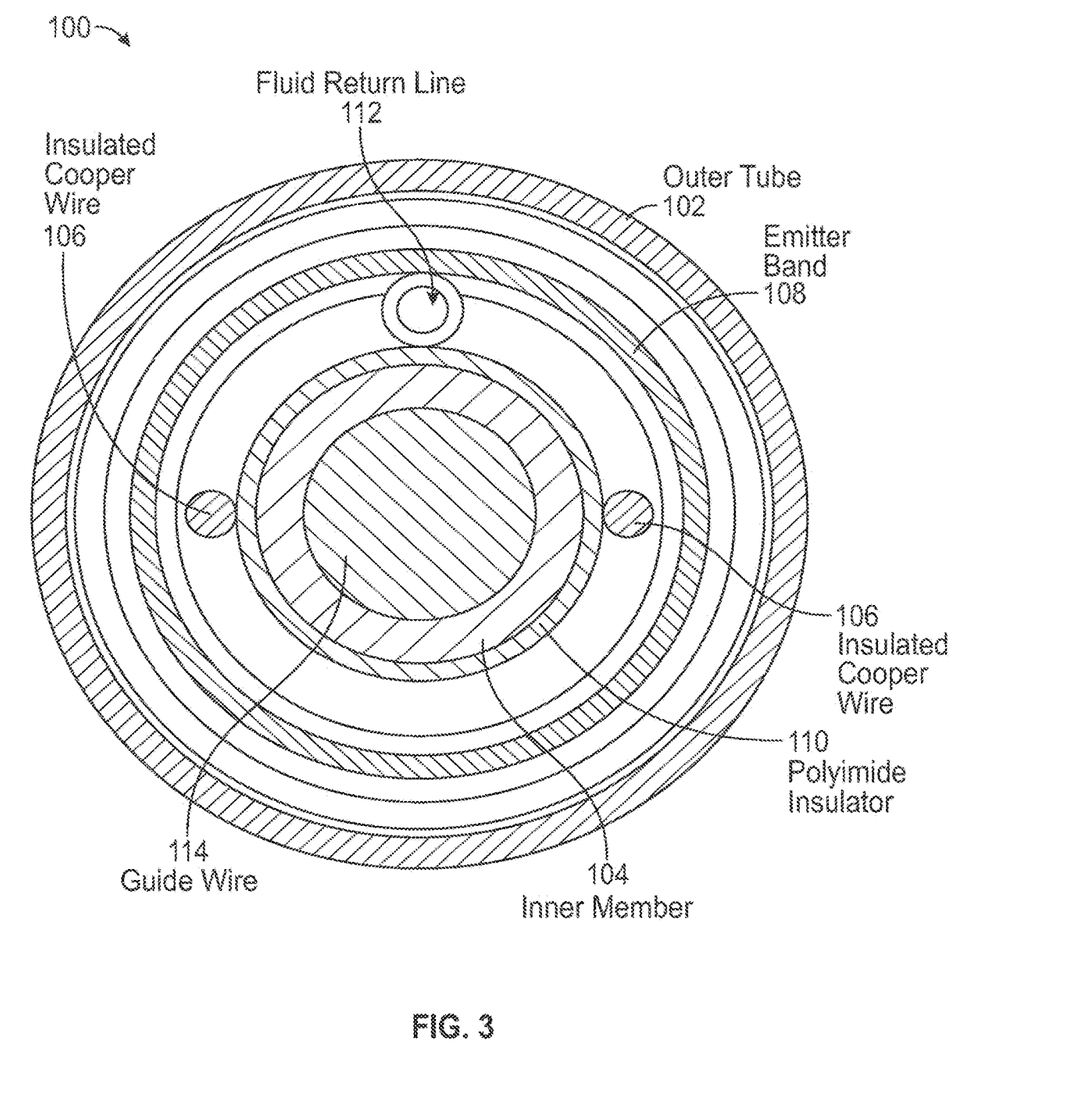
FIG. 3 depicts a front sectional view of an example shock wave device for generating forward directed shock waves, in accordance with some embodiments.

FIG. 1 depicts a cutaway perspective view of an example shock wave device 100 for generating forward directed shock waves, in accordance with some embodiments. The device 100 includes an outer covering 102 (e.g., a flexible outer tube) and an inner member 104 that forms a lumen for a guide wire 114. The outer covering 102 and inner member 104 are connected at a distal end of the device 100, where the guide wire 114 may exit the device 100. The interior volume of the device 100 between the outer covering 102 and inner member 104 may be filled with a conductive fluid (e.g., saline and/or imaging contrast agent). Two insulated conductive wires 106 (e.g., insulated copper wires) extend along the length of the device 100 within the interior volume. While only one wire 106 is visible in FIG. 1, the second wire 106 extends along an opposing side of the inner member 104, as shown in FIGS. 2-3. The two wires 106 end near the distal end of the device 100 where the guide wire exits the lumen formed by the inner member 104. The ends of the two wires 106 include uninsulated portions (not shown). For example, the flat circular surfaces at the ends of the two wires may be uninsulated. An emitter band 108 is positioned within the interior volume around the ends of the two wires 106. The emitter band 108 may be a conductive cylinder with a diameter larger than the total diameter of the inner member 104 and the two wires 106 combined, such that the emitter band circumscribes the ends of the two wires 106 without contacting the wires, as shown in FIG. 2. An insulating sheath 110 (e.g., a polyimide insulator) may be positioned around the inner member 104 to separate the two wires 106 from the inner member 104 and to further insulate the two wires 106 from one another. In this way, the preferred conductive path between the two wires 106 is through the emitter band 108. When a high voltage pulse is applied across the two wires 106, an electrical current will arc from the uninsulated end of one wire to the emitter band 108, and then arc again from the emitter band 108 to the uninsulated end of the other wire. As a result, shock waves are initiated at the distal end of the shock wave device 100, which then propagate through the conductive fluid and the wall of the outer covering 102 to impinge on an occlusion or calcification.

In some embodiments, the device 100 may include a second pair of wires (not shown) offset from wires 106 by 90 degrees. For example, if wires 106 are positioned at 0 and 180 degrees, the second pair of wires may be positioned at 90 and 270 degrees. The second pair of wires also end near the distal end of the device 100 and include uninsulated portions at their ends. The emitter band 108 circumscribes the ends of the second pair of wires as well. A separate high voltage pulse may be applied across the second pair of wires to generate a second pair of arcs with the emitter band 108. As a result, a second set of shock waves are initiated from the distal end of the device 100. The first pair of wires 106 and the second pair of wires may be activated alternately, which may improve the effectiveness of the device 100 by further spreading the shock waves.

A fluid return line 112 with an inlet near the distal end of the device 100 draws in the conductive fluid from the interior volume, while a fluid pump (not shown) pumps in additional conductive fluid via a fluid inlet (shown in FIG. 5) at a proximal end of the device 100. In this way, the fluid return line 112 and fluid pump circulate the conductive fluid under pressure within the interior volume. Circulation of the conductive fluid may prevent bubbles created by the device 100 from becoming trapped within the distal tip of the device 100 due to the limited space within the tip. Furthermore, circulation of the conductive fluid may aid in cooling the device 100 and treatment site.

FIG. 2 depicts a side sectional view of an example shock wave device 100 for generating forward directed shock waves, in accordance with some embodiments. As shown in FIG. 2, the two conductive wires 106 (e.g., polyimide-insulated copper wires) are positioned along opposing sides of the inner member 104. Each of the wires 106 include uninsulated wire ends 202. The insulating sheath 110 (e.g., polyimide tubing) is positioned in a region proximate to the uninsulated wire ends 202 to decrease the likelihood of electrical current arcing from one wire end to the other. The emitter band 108 is positioned with a forward edge closer to the distal end of the device 100 than the wire ends 202, such that two spark gaps are formed between each of the wire ends 202 and the emitter band 108. The positioning of the wire ends 202, insulating sheath 110, and emitter band 108 makes it so that when a high voltage pulse is applied across the two wires 106, an electrical current will arc from the uninsulated end of one wire to the emitter band 108, and then arc again from the emitter band 108 to the uninsulated end of the other wire. As a result, shock waves are initiated at the distal end of the shock wave device 100, which then propagate through the conductive fluid and the wall of the outer covering 102 to impinge on an occlusion or calcification. The positioning of the emitter band 108 closer to the distal end of the device than the wire ends 202 helps to encourage the shock waves to propagate in a substantially forward direction (e.g., longitudinally out of the distal end of the device 100). Shock waves may be generated repeatedly, as may be desirable by the practitioner to treat a region of vasculature.

FIG. 3 depicts a front sectional view of an example shock wave device 100 for generating forward directed shock waves, in accordance with some embodiments. As shown in FIG. 3, the emitter band 108 circumscribes the two conductive wires 106 (e.g., insulated copper wires) and the fluid return line 112. The fluid return line 112 includes an inlet that draws in conductive fluid from the interior volume of the device to allow the conductive fluid to be circulated within the distal end of the device 100.

Figure 4:
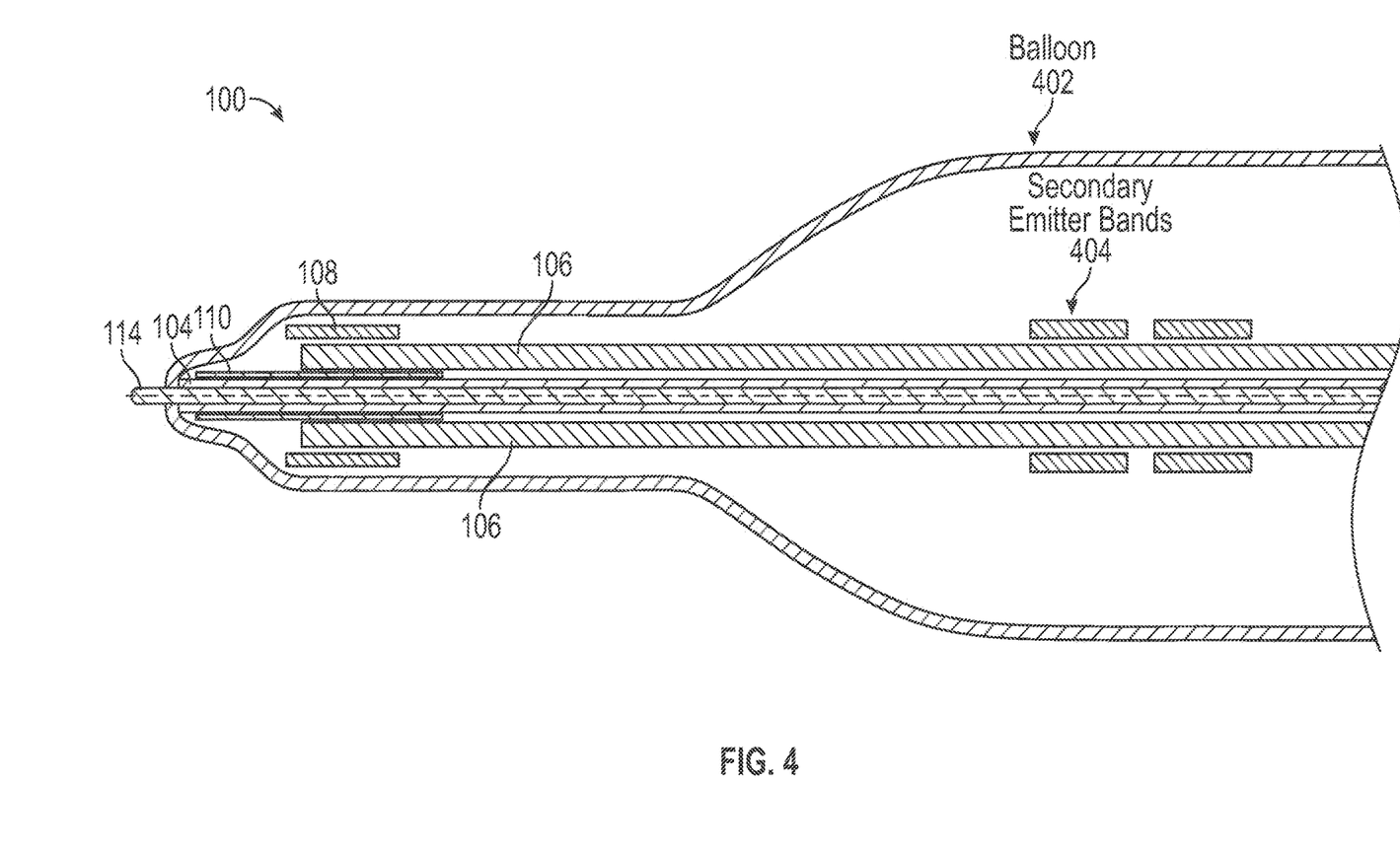
FIG. 4 depicts an extended side sectional view of an example shock wave device for generating forward directed shock waves, in accordance with some embodiments.

FIG. 4 depicts an extended side sectional view of an example shock wave device 100 for generating forward directed shock waves, in accordance with some embodiments. As shown in FIG. 4, in some embodiments, the outer covering of the device 100 includes an angioplasty balloon 402. The balloon 402 may be inflated by pumping additional fluid into the interior volume of the device. The balloon 402 may be inflated before or after applying shock waves to a treatment region. For example, in some embodiments, after forward directed shock waves are initiated using the emitter band 108 at the distal end of the device 100 to break apart an occlusion, the device 100 is advanced further into a patient's vascular, and the balloon 402 is inflated in the region of the occlusion to further treat the region.

In some embodiments, the shock wave device 100 may include secondary emitter bands 404 located in a medial location of the device 100. The device 100 shown in FIG. 4 includes two secondary emitter bands 404, but various numbers of secondary bands 404 may be used. For example, in some embodiments, the device 100 may include a single secondary emitter band 404. In other embodiments, the device 100 may include five or more secondary emitter bands 404. The secondary emitter bands 404 may generate shock waves using a variety of techniques. For example, the secondary emitter bands 404 may generate shock waves using low-profile or coplanar electrodes, such as those described in U.S. Pat. No. 8,888,788 and U.S. application Ser. No. 15/346,132, which are hereby incorporated by reference in their entireties. The shock waves may radiate in a substantially radial direction from the medial location of the secondary emitter bands 404. In some embodiments, the secondary emitter bands 404 may initiate shock waves independently of the emitter band 108 at the distal end of the device 100. For example, in some embodiments, after forward directed shock waves are initiated using the emitter band 108 at the distal end of the device 100 to break apart an occlusion, the device 100 is advanced further into a patient's vascular until the medial location of a secondary emitter band 404 is aligned with the region of the occlusion. Then additional shock waves may be initiated from the secondary emitter band 404 to further treat the region. In order to permit independent operation, additional conductive wires may be provided between the high voltage source and the second emitter bands 404.

In some embodiments, forward directed shock waves from the emitter band 108, radial directed shock waves from the secondary emitter bands 404, and inflation of the angioplasty balloon 402 may be utilized in various sequences and combinations to treat plaques or obstructions in vessels. The vessels may include blood vessels in a patient's vascular system or ureters in the patient's urinary system.

Figure 5:
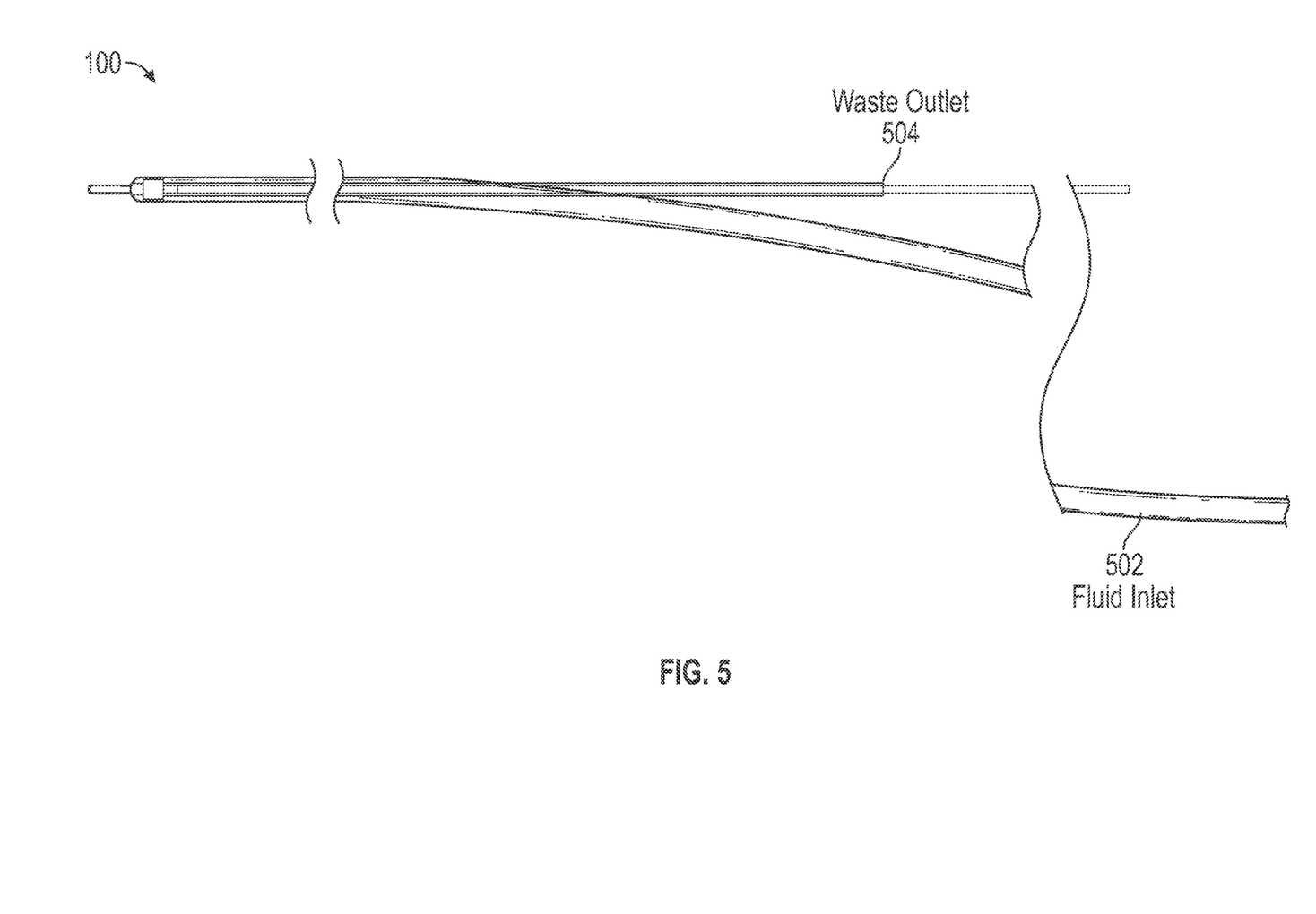
FIG. 5 depicts a side view of an extended length of an example shock wave device, in accordance with some embodiments.

FIG. 5 depicts a side view of an extended length of an example shock wave device 100, in accordance with some embodiments. The shock wave device 100 may be in communication with a fluid source and fluid pump (not shown) that introduces conductive fluid into an interior volume of the device 100 via a fluid inlet 502. The fluid pump may fill the interior volume with fluid to a certain pressure. The conductive fluid may be circulated within the interior volume of the device 100 by drawing fluid into the fluid return line shown in FIGS. 1 and 3, and then dispelling it through a waste outlet 504. The waste outlet 504 may include a pressure relief valve to maintain the fluid pressure within the interior volume of the device while the conductive fluid is circulated. Circulation of the conductive fluid may prevent bubbles created by the device 100 from becoming trapped within the distal tip of the device 100 due to the limited space within the tip. Trapped bubbles may block subsequent shock waves from propagating from the device 100, thus it is beneficial to prevent their build-up. In some embodiments, the waste outlet 504 may be connected to the fluid source so that the fluid pump recirculates the waste fluid.

Figure 6:
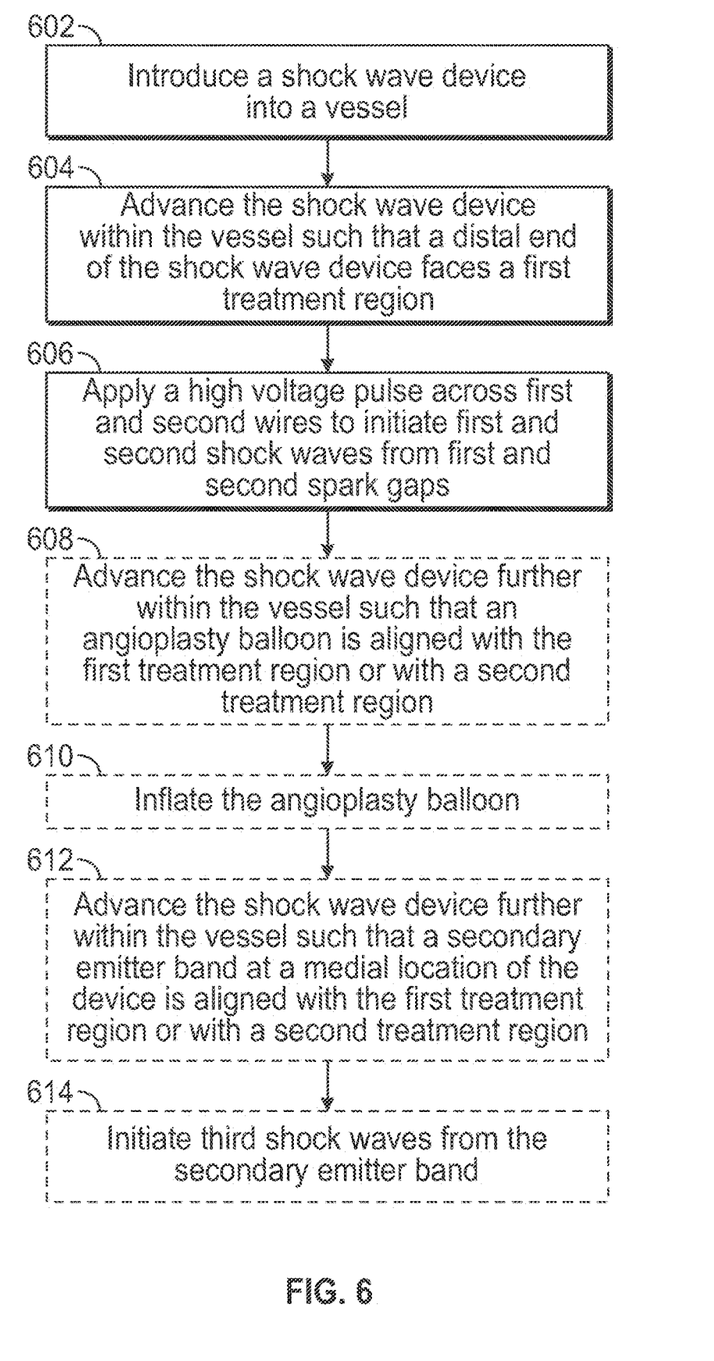
FIG. 6 is a flowchart representation of an exemplary method for generating forward directed shock waves.

FIG. 6 is a flowchart representation of an exemplary method for generating forward directed shock waves. As depicted in FIG. 6, a shock wave device is introduced into a vessel (602). The vessel may include blood vessels in a patient's vascular system or ureters in the patient's urinary system. The shock wave device may be the device 100 described in reference to FIGS. 1-5. The shock wave device is advanced within the vessel such that a distal end of the device faces a first treatment region (604). The first treatment region may include a chronic total occlusion (CTO), circumferential calcium, a kidney stone, or other obstructions or concretions. Once the distal end of the shock wave device is facing the first treatment region, a high voltage pulse is applied across first and second wires to initiate first and second shock waves from first and second spark gaps formed between the first and second wires and an emitter band (606). Due to the positioning of the first and second wires and the emitter band, the first and second shock waves propagate in a substantially forward direction out of the shock wave device to impinge on the occlusion or calcium in the first treatment area. In some embodiments, the shock wave device may then be advanced further within the vessel such that an angioplasty balloon is aligned with the first treatment region or with a second treatment region (608). The angioplasty balloon may then be inflated in the first or second treatment regions (610). In this way, conventional angioplasty balloon treatments may be applied to treat one or more treatment regions after the shock wave treatments are applied. Alternatively or in addition, in some embodiments, the shock wave device may be advanced further within the vessel such that a secondary emitter band at a medial location of the device is aligned with the first treatment region or with a second treatment region (612). Third shock waves may then be initiated from the secondary emitter band to apply additional shock wave treatment to the first or second treatment areas (614). Steps 604-614 may be carried out in various sequences or combinations, and repeated as necessary, when appropriate to treat the patient.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A catheter for treating occlusions in blood vessels, comprising:
   a tubular inner member;
   an emitter assembly comprising:
   a first insulated wire extending along a length of the tubular inner member with an uninsulated distal face;
   a second insulated wire extending along the length of the tubular inner member having an uninsulated distal face, the second insulated wire being circumferentially offset from the first insulated wire;
   an electrically conductive sheath wrapped circumferentially around the first insulated wire and the second insulated wire with a first spark gap extending between the electrically conductive sheath and the distal face of the first insulated wire and a second spark gap extending between the electrically conductive sheath and the distal face of the second insulated wire; and
   a flexible member sealably attached to a distal end of the catheter and surrounding the emitter assembly, said flexible member being fillable with conductive fluid, wherein when the flexible member is filled with the conductive fluid and an electrical pulse is applied across the first and second wires, first and second shock waves will be initiated from the first and second spark gaps.

2. The catheter of claim 1, wherein the second insulated wire is circumferentially offset from the first insulated wire by 180 degrees.

3. The catheter of claim 1, wherein a distal end of the conductive sheath extends distally beyond the distal face of the first insulated wire and the distal face of the second insulated wire.

4. The catheter of claim 1, wherein a distal end of the conductive sheath is proximate to the distal face of the first insulated wire and the distal face of the second insulated wire.

5. The catheter of claim 1, comprising an insulating sheath circumscribing the tubular inner member in a region proximate to the distal face of the first insulated wire and the distal face of the second insulated wire.

6. The catheter of claim 1, comprising:
   a fluid pump connected to a proximal end of the catheter configured to provide the conductive fluid to fill the flexible member; and
   a fluid return line having an inlet proximate to the distal end of the catheter and configured to remove the conductive fluid from the flexible member, wherein the fluid pump and the fluid return line are configured to circulate the conductive fluid under pressure inside the flexible member.

7. The catheter of claim 6, comprising a pressure relief valve at an outlet of the fluid return line.

8. The catheter of claim 1, wherein the conductive fluid comprises saline or a combination of saline and a contrasting agent.

9. The catheter of claim 1, comprising one or more secondary conductive sheaths disposed at a medial location of the tubular inner member and configured to initiate shock waves from the medial location.

10. The catheter of claim 1, wherein the tubular inner member comprises a guide wire lumen.

11. The catheter of claim 1, comprising:
a third insulated wire extending along a length of the tubular inner member with an uninsulated distal face;
a fourth insulated wire extending along the length of the tubular inner member having an uninsulated distal face, the fourth insulated wire being circumferentially offset from the third insulated wire; and
wherein the conductive sheath is wrapped circumferentially around the third insulated wire and the fourth insulated wire with a third spark gap extending between the conductive sheath and the distal face of the third insulated wire and a fourth spark gap extending between the conductive sheath and the distal face of the fourth insulated wire.

12. The catheter of claim 11, wherein the fourth insulated wire is circumferentially offset from the third insulated wire by 180 degrees.

13. The catheter of claim 12, wherein the third insulated wire is circumferentially offset from the first insulated wire by 90 degrees.

14. A method for treating occlusions in blood vessels, comprising:
introducing a catheter into a patient's vasculature, the catheter comprising:
a tubular inner member;
an emitter assembly comprising:
a first insulated wire extending along a length of the tubular inner member with an uninsulated distal face;
a second insulated wire extending along the length of the tubular inner member having an uninsulated distal face, the second insulated wire being circumferentially offset from the first insulated wire;
an electrically conductive sheath wrapped circumferentially around the first insulated wire and the second insulated wire with a first spark gap extending between the electrically conductive sheath and the distal face of the first insulated wire and a second spark gap extending between the electrically conductive sheath and the distal face of the second insulated wire;
a flexible member sealably attached to the distal end of the catheter and surrounding the emitter assembly, said flexible member being fillable with conductive fluid;
advancing the catheter within the vasculature such that the distal end of the catheter is aligned with a first treatment region;
filling the flexible member with the conductive fluid; and
applying an electrical pulse across the first and second conductive wires to initiate first and second shock waves from the first and second spark gaps.

15. The method of claim 14, wherein the second insulated wire is circumferentially offset from the first insulated wire by 180 degrees.

* * * * *